United States Patent
Arai et al.

(10) Patent No.: US 9,393,133 B2
(45) Date of Patent: Jul. 19, 2016

(54) ABDOMINAL CAVITY-VEIN SHUNT STENT

(75) Inventors: Yasuaki Arai, Tokyo (JP); Shinichi Sakai, Yokohama (JP)

(73) Assignees: PIOLAX MEDICAL DEVICES, INC., Yokohama-shi, Kanagawa (JP); NATIONAL CANCER CENTER, Tokyo (JP)

(*) Notice: Subject to any disclaimer, the term of this patent is extended or adjusted under 35 U.S.C. 154(b) by 53 days.

(21) Appl. No.: 14/000,090

(22) PCT Filed: Feb. 18, 2011

(86) PCT No.: PCT/JP2011/053468
§ 371 (c)(1),
(2), (4) Date: Aug. 16, 2013

(87) PCT Pub. No.: WO2012/111137
PCT Pub. Date: Aug. 23, 2012

(65) Prior Publication Data
US 2013/0325103 A1 Dec. 5, 2013

(51) Int. Cl.
*A61F 2/82* (2013.01)
*A61F 2/24* (2006.01)
(Continued)

(52) U.S. Cl.
CPC .................. *A61F 2/82* (2013.01); *A61F 2/2418* (2013.01); *A61F 2/2475* (2013.01); *A61M 39/22* (2013.01);
(Continued)

(58) Field of Classification Search
CPC ... A61F 2/2475; A61F 2/2418; A61F 2/2412; A61F 2/82; A61F 9/00781; A61F 2/07; A61M 27/002; A61M 27/008; A61M 27/006; A61M 39/22

USPC .................................................. 623/1.24–1.26
See application file for complete search history.

(56) References Cited

U.S. PATENT DOCUMENTS 5,409,019 A * 4/1995 Wilk .............................. 128/898
5,655,548 A * 8/1997 Nelson ............ A61B 17/320016
128/898

(Continued)

FOREIGN PATENT DOCUMENTS

JP 2000-505316 A 5/2000
JP 2001-527440 A 12/2001
(Continued)

OTHER PUBLICATIONS

Klabunde, "Cardiovascular Physiology Concepts", located at http://www.cyphysiology.com/Heart%20Disease/HD004.htm, (Nov. 2012).*
(Continued)

*Primary Examiner* — Paul Prebilic
(74) *Attorney, Agent, or Firm* — McGinn IP Law Group PLLC (57) ABSTRACT

An abdominal cavity-vein shunt stent provided for transporting ascites accumulated in the abdominal cavity of a patient to a vascular system, includes: a stent body which extends cylindrically long and which has one end disposed in the intrahepatic vein, and the other end piercing the liver parenchyma and disposed in the abdominal cavity; and a one-way valve which is disposed in the stent body, which is opened to drain ascites into the intrahepatic vein when a differential pressure obtained by subtracting the pressure of the intrahepatic vein from the pressure in the abdominal cavity is not lower than a predetermined value, and which is closed when the differential pressure is lower than the predetermined value.

12 Claims, 5 Drawing Sheets

(51) Int. Cl.
*A61M 39/22* (2006.01)
*A61M 27/00* (2006.01)
*A61F 2/07* (2013.01)
*A61F 2/90* (2013.01)

(52) U.S. Cl.
CPC .... *A61F 2/07* (2013.01); *A61F 2/90* (2013.01); *A61F 2220/005* (2013.01); *A61F 2220/0058* (2013.01); *A61M 27/002* (2013.01); *A61M 2202/0401* (2013.01)

(56) References Cited

U.S. PATENT DOCUMENTS

| | | | | |
|---|---|---|---|---|
| 5,830,222 | A * | 11/1998 | Makower | A61B 1/3137 604/99.03 |
| 6,090,140 | A * | 7/2000 | Gabbay | 623/2.1 |
| 6,162,245 | A * | 12/2000 | Jayaraman | 623/1.15 |
| 6,196,230 | B1 | 3/2001 | Hall et al. | |
| 6,261,304 | B1 * | 7/2001 | Hall et al. | 606/194 |
| 6,616,675 | B1 | 9/2003 | Evard et al. | |
| 6,790,237 | B2 * | 9/2004 | Stinson | A61F 2/04 623/1.24 |
| 7,159,592 | B1 | 1/2007 | Makower et al. | |
| 7,270,675 | B2 * | 9/2007 | Chun | A61F 2/2412 623/1.15 |
| 7,628,804 | B2 * | 12/2009 | Flagle | A61F 2/07 623/1.24 |
| 9,021,670 | B2 * | 5/2015 | Dale et al. | 29/235 |
| 9,220,594 | B2 * | 12/2015 | Braido | A61F 2/2412 |
| 2001/0007956 | A1 * | 7/2001 | Letac et al. | 623/2.11 |
| 2002/0042564 | A1 | 4/2002 | Cooper et al. | |
| 2002/0062146 | A1 | 5/2002 | Makower et al. | |
| 2002/0165606 | A1 * | 11/2002 | Wolf et al. | 623/1.24 |
| 2002/0198588 | A1 | 12/2002 | Armstrong et al. | |
| 2003/0069646 | A1 * | 4/2003 | Stinson | 623/23.7 |
| 2003/0114913 | A1 * | 6/2003 | Spenser | A61F 2/2412 623/1.11 |
| 2003/0163079 | A1 * | 8/2003 | Burnett | 604/9 |
| 2004/0044402 | A1 * | 3/2004 | Jung et al. | 623/1.24 |
| 2004/0210307 | A1 * | 10/2004 | Khairkhahan | 623/2.18 |
| 2009/0030511 | A1 * | 1/2009 | Paniagua | A61F 2/2412 623/2.13 |
| 2009/0281557 | A1 | 11/2009 | Sander et al. | |
| 2015/0032206 | A1 * | 1/2015 | Alkhatib | 623/2.18 |
| 2015/0100119 | A1 * | 4/2015 | Li et al. | 623/2.18 |

FOREIGN PATENT DOCUMENTS

| | | |
|---|---|---|
| JP | 2002-369880 A | 12/2002 |
| JP | 2003-500121 A | 1/2003 |
| JP | 2003-506132 A | 2/2003 |
| JP | 2006-507018 A | 3/2006 |
| JP | 2006-116184 A | 5/2006 |
| JP | 2009-201867 A | 9/2009 |
| JP | 4480919 B1 | 6/2010 |
| WO | WO 97/27898 A1 | 8/1997 |
| WO | WO 98/46115 A1 | 10/1998 |
| WO | WO 00/71195 A1 | 11/2000 |
| WO | WO 01/10314 A1 | 2/2001 |
| WO | WO 03/072166 A1 | 9/2003 |
| WO | WO 2009045331 A1 * | 4/2009 ............ A61F 2/24 |

OTHER PUBLICATIONS

International Search Report (ISR) (PCT Form PCT/ISA/210), in PCT/JP2011/053468, dated May 24, 2011.

Extended European Search Report dated Mar. 18, 2016.

* cited by examiner

ABDOMINAL CAVITY-VEIN SHUNT STENT

TECHNICAL FIELD

The present invention relates to an abdominal cavity-vein shunt stent for transporting ascites accumulated in the abdominal cavity of a patient to a vascular system.

BACKGROUND ART

Ascites may be accumulated in the abdominal cavity because of peritonitis, cirrhosis, cancer, etc. Among various measures to deal with the ascites, one measure is to reduce ascites by forcibly draining water in the body as urine using diuretics, and another measure is to directly remove ascites by inserting a tube in the abdominal cavity. However, since ascites includes leukocytes, proteins, etc., it is not preferable in many cases that ascites is drained from the body simply.

Therefore, a method of placing a catheter in the body for the purpose of returning ascites back into the body without draining the ascites has been put into practical use. The abdominal cavity-vein shunt catheter has a chamber provided with a check valve, a venous tube connected to one end of the chamber, and an abdominal cavity tube connected to the other end of the chamber.

To place the abdominal cavity-vein shunt catheter, first, a pocket for placing the chamber is provided by puncturing the subclavian vein, and a distal end of the venous tube is attached to an insertion jig called tunneler. Then, the tunneler is inserted from a predetermined portion of the abdominal cavity and pushed through the hypodermis, the chamber is placed in the pocket, and the distal end of the venous tube is inserted into the vena cava via the subclavian vein while the abdominal cavity tube is placed in the abdominal cavity. When the pressure in the abdominal cavity increases, the check valve of the chamber is opened, thereby transporting ascites to the vein.

In the abdominal cavity-vein shunt catheter, because the placement range thereof is wide and the tunneler is pushed through the hypodermis, the physical load imposed on the patient is heavy. Further, there is a possibility that the catheter may be damaged by body motion, an external injury, etc.

In view of above, the present applicant has devised an abdominal cavity-vein shunt catheter to lighten the physical load imposed on a patient. Patent Literature 1 discloses, as such a catheter, an abdominal cavity-vein shunt catheter which has an ascites inlet provided at one end portion and/or at a side portion near one end portion, an outlet provided at an intermediate portion to communicate with the right atrium or the vena cava, and a check valve provided in the outlet so as to be opened when the catheter internal pressure compared with the external pressure is higher than a predetermined value but to be closed when the catheter internal pressure is lower than the predetermined value. The catheter is implanted in the body such that the catheter is inserted from the right subclavian vein to pierce the liver through the right atrium, the vena cava and the right hepatic vein and to be led into the peritoneal cavity, and the other end is closed after the implantation. Thus, the catheter is used in the condition that the inlet is placed in the peritoneal cavity while the outlet is located in the vein.

According to the abdominal cavity-vein shunt catheter, because the catheter can be implanted in a relatively narrow range of from the right subclavian vein to the peritoneal cavity without passing through the hypodermal tissue, the physical load imposed on a patient at the time of placement of the catheter can be lightened significantly compared with the background-art abdominal cavity-vein shunt catheter placed through the hypodermis.

CITATION LIST

Patent Literature

Patent Literature 1
JP-4480919-B

SUMMARY OF INVENTION

Technical Problem

In the background-art abdominal cavity-vein shunt catheter, because a long tube-like catheter is placed in a wide range of from the subclavian vein to the abdominal cavity, the load imposed on a patient after placement of the catheter is heavy.

In the aforementioned abdominal cavity-vein shunt catheter of Patent Literature 1, because the catheter is placed in a path in which the catheter is inserted from the subclavian vein, pierces directly the liver and reaches the abdominal cavity, the catheter can be placed in a narrow range in the body compared with the background-art abdominal cavity-vein shunt catheter so that the load imposed on the patient after placement of the catheter is relatively light. However, since there is still the load on the patient as a result of placing the long tube-like catheter gives, it is desired that the load imposed on the patient after placement of the catheter can be lightened more.

An object of the invention is to provide an abdominal cavity-vein shunt stent in which excessive ascites accumulated in the abdominal cavity can be surely transported into the vein and in which the load imposed on a patient can be minimized not only at the time of placement in the body but also after placement in the body.

Solution to Problem

To achieve the foregoing object, the invention provides a stent for transporting ascites accumulated in the abdominal cavity of a patient to a vascular system, including:

a cylindrically-extending stent body which has one end disposed in an intrahepatic vein and the other end disposed in the abdominal cavity by piercing a liver parenchyma; and a one-way valve which is disposed in the stent body, which is opened to drain the ascites into the intrahepatic vein when a differential pressure obtained by subtracting a pressure of the intrahepatic vein from a pressure in the abdominal cavity is not lower than a predetermined value, and which is closed when the differential pressure is lower than the predetermined value.

The invention may provide the abdominal cavity-vein shunt stent, wherein an entrance preventing member which prevents organs in the abdominal cavity from entering the stent body is provided in an opening of the other end of the stent body which is disposed in the abdominal cavity.

The invention may provide the abdominal cavity-vein shunt stent, wherein a cover member which prevents the liver parenchyma from entering the stent body is arranged in a portion of the stent body which passes through the liver parenchyma.

The invention may provide the abdominal cavity-vein shunt stent, wherein a portion of the stent body which is disposed in the intrahepatic vein is shaped like mesh.

The invention may provide the abdominal cavity-vein shunt stent,
wherein a stent recovery handle is provided at the one end of the stent body which is disposed in the intrahepatic vein.

The invention may provide the abdominal cavity-vein shunt stent,
wherein the cover member and the one-way valve are formed integrally and are disposed on an inner circumferential side of the stent body.

Advantageous Effects of Invention

According to the invention, when the differential pressure obtained by subtracting the pressure of the intrahepatic vein from the pressure in the abdominal cavity becomes not lower than the predetermined value due to accumulation of ascites in the abdominal cavity, the one-way valve is opened to drain the ascites into the intrahepatic vein so that excessive ascites accumulated in the abdominal cavity can be transported. When the differential pressure becomes lower than the predetermined value, the one-way valve is closed to prevent the blood flowing in the intrahepatic vein from flowing out to the abdominal cavity side. In this manner, the pressure in the abdominal cavity can be kept at a constant value.

The stent may function well as long as one end of the stent body is disposed in the intrahepatic vein and the other end of the stent body passes through the liver parenchyma so as to be disposed in the abdominal cavity. Because the stent can be placed by an intravascular operation performed by a guide wire, a catheter or the like, the load imposed on the patient at the time of placement of the stent can be lightened. Because one end of the stent body is disposed in the intrahepatic vein and the other end of the stent body is disposed in the abdominal cavity near the liver, the stent is relatively short so that the load imposed on the patient after placement of the stent can be lightened.

BRIEF DESCRIPTION OF DRAWINGS

FIG. 1 A view showing an embodiment of an abdominal cavity-vein shunt stent according to the invention, in which (a) is a perspective view of the stent, and (b) is a perspective view seen from an angle different from (a).

FIG. 2 (a) is a front view of the stent, (b) is a right side view of the stent, and (c) is a left side view of the stent.

FIG. 4 An explanatory view showing a state when the pressure in the abdominal cavity is not higher than a predetermined value in the condition that the stent is used, in which (a) is an explanatory view showing a state where the stent is placed, and (b) is an end view seen from the insertion side of the stent into the intrahepatic vein.

FIG. 5 An explanatory view showing a state when the pressure in the abdominal cavity is higher than the predetermined value in the condition that the stent is used, in which (a) is an explanatory view showing a state where the stent is placed, and (b) is an end view seen from the insertion side of the stent into the intrahepatic vein.

DESCRIPTION OF EMBODIMENTS

An embodiment of an abdominal cavity-vein shunt stent according to the invention will be described below with reference to the drawings.

Figure 3:
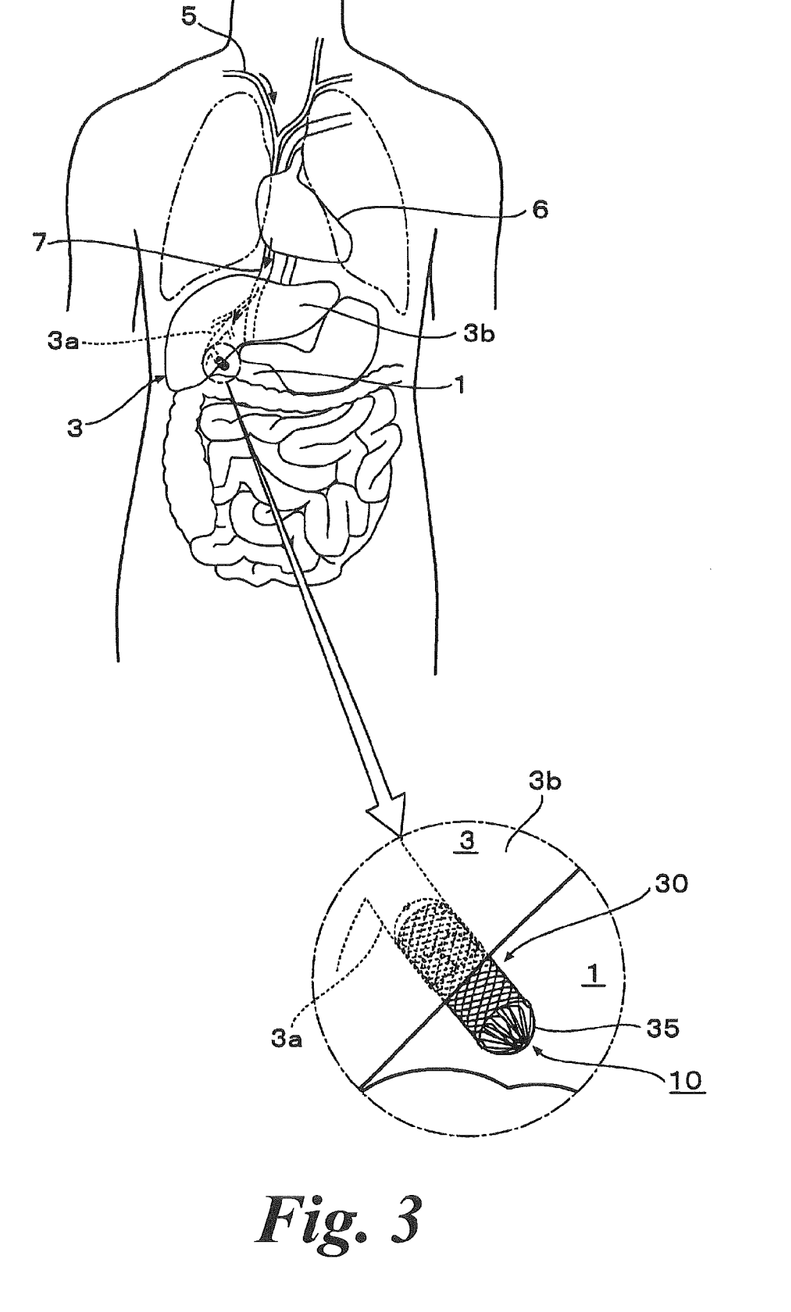
FIG. 3 An explanatory view showing a state where the stent is placed in the body.

As shown in FIGS. 3 and 4, the abdominal cavity-vein shunt stent 10 ("stent 10") is provided for transporting ascites accumulated in the inside of the abdominal cavity 1 to a vascular system. The stent 10 extends cylindrically long and has a stent body 30 which has one end to be disposed in the intrahepatic vein 3a of the liver 3, and the other end for passing through the liver parenchyma 3b to be disposed in the abdominal cavity 1.

Referring also to FIGS. 1 and 2, the stent body 30 in this embodiment is formed into a cylindrical shape by braiding and/or enlacing wire 31 having a predetermined diameter. The stent body 30 is shaped like mesh having a predetermined pattern, and is of a so-called self-expanding type, that is, diametrically contracts with application of external force but diametrically expands in the free state without any external force.

Metal wire of stainless steel, Ta, Ti, Pt, Au, W, or the like, is preferred as the material of the wire 31. Particularly, a shape memory alloy enabling to give a shape memory effect by heat treatment and superelasticity can be used preferably. An Ni—Ti-based alloy, a Cu—Zn—X (X=Al, Fe, etc.) alloy, an Ni—Ti—X (X=Fe, Cu, V, Co, etc.) alloy, or the like, may be used preferably as the shape memory alloy. The outer surface of the wire 31 may be coated with Au, Pt or the like to give radiopacity. A synthetic resin fiber or the like may be used as the wire 31. The stent body 30 is not limited to the self-expanding type, and there may be used the stent body 30 which is diametrically expanded by a balloon or the like.

The stent body 30 may be formed by cutting a thin cylindrical body of any one of the aforementioned various metals (stainless steel, Ni—Ti-based alloy, etc.) into a predetermined mesh pattern by laser processing, etching or the like.

An entrance preventing member 35 for preventing organs (such as the intestines) in the abdominal cavity 1 from entering the stent body 30 is provided in the other end side opening of the stent body 30 disposed in the abdominal cavity 1. As shown in FIG. 1(b) and FIG. 2(b), the entrance preventing member 35 in this embodiment is formed into a mesh shape by braiding and/or enlacing the wire 31 so as to be integral with the stent body 30. The entrance preventing member 35 is narrowed gradually while extending in the axial direction from the circumferential edge of the other end side opening of the stent body 30, and an opening 35a is provided at a distal end. The entrance preventing member 35 can permit passage of ascites while preventing entrance of the organs. The entrance preventing member 35 is not limited to the aforementioned shape. For example, the entrance preventing member 35 may be formed into a crosswise shape to block the other end side opening of the stent body 30.

A recovery handle 37 is provided at one end of the stent body 30 to be disposed in the intrahepatic vein 3a so that, when the stent 10 is placed in the body, the stent 10 can be recovered by engaging a clamp-shape or J-hook-shape stent recovery jig with the recovery handle 37. In this embodiment, the recovery handle 37 is formed by bending like a circular arc having two ends connected to opposite places of the circumferential edge of the one end side opening of the stent body 30, respectively. The recovery handle 37 may be formed into a toric shape, a hook shape or the like. The shape of the recovery handle 37 is not particularly limited as long as the stent recovery jig can be engaged with the recovery handle 37.

Markers 39 of a radiopaque metal such as Au, Pt or Pd are fixed to predetermined places of the stent body 30 so that the stent 10 can be visually recognized under a fluoroscope. In this embodiment, such markers 39 are provided at the intermediate portion of the stent body 30, the other end side circumferential edge of the stent body 30, the entrance preventing member 35, the one end side circumferential edge of the stent body 30 and the recovery handle 37, respectively.

Figure 2A:
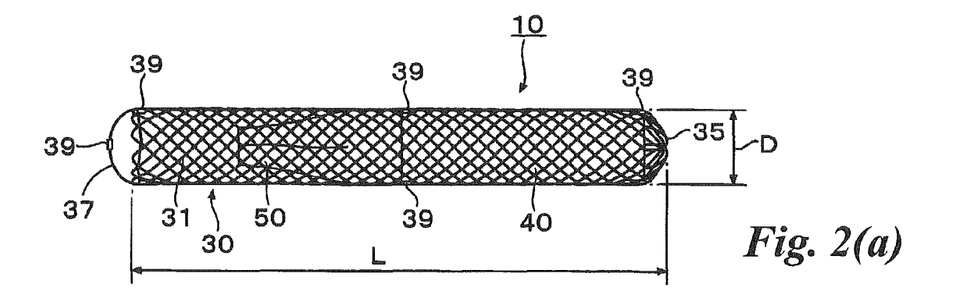

As shown in FIG. 2(a), the total length L of the stent body 30 (the length from the distal end of the entrance preventing member 35 to one end of the stent body 30 except the recovery handle 37) is preferably in a range of 20 to 100 mm, more preferably in a range of 40 to 50 mm. The outer diameter D of the stent body 30 in the diametrically-expanded state without any external force is preferably in a range of 3 to 15 mm, more preferably in a range of 5 to 7 mm.

As described above, the stent body 30 passes through the liver parenchyma 3b such that the other end of the stent body 30 is disposed in the abdominal cavity 1 (see FIGS. 3 and 4). A cover member 40 for preventing the liver parenchyma 3b from entering the stent body 30 is disposed in a portion of the stent body 30 passing through the liver parenchyma 3b.

In this embodiment, the cover member 40 is substantially shaped like a cylinder. The cover member 40 extends with a predetermined length along the axial direction from the portion of the stent body 30 passing through the liver parenchyma, that is, from the other end side opening of the stent body 30 provided with the entrance preventing member 35, and is fixed to the inner circumferential side of the stent body 30 by dipping molding or heat welding or by an adhesive agent or the like so that the mesh portion of the stent body 30 is blocked with the cover member 40. The cover member 40 may be fixed to the outer circumferential side of the liver parenchyma passage portion of the stent body 30.

On the other hand, the other portion of the stent body 30 than the liver parenchyma passage portion, that is, the portion where the cover member 40 is not disposed, is opened like mesh so that fluids such as ascites, blood, etc. can flow into and out of the stent body 30 through the openings of the mesh.

As the material of the cover member 40, a synthetic resin having flexibility, such as polyethylene, polypropylene, polyvinyl chloride, polyvinyl acetate, polyurethane, polystyrene, polyamide, silicone, etc. may be listed and a mixture or copolymer thereof may be used. A fluorine-based resin such as polytetrafluoroethylene (PTFE), perfluoroalkoxy resin (PFA), tetrafluoroethylene-hexafluoropropylene copolymer (FEP), tetrafluoroethylene-ethylene copolymer (ETFE), etc. or natural rubber may be used.

The stent 10 has a one-way valve 50 which is disposed in the stent body 30. The one-way valve 50 is opened to drain ascites into the intrahepatic vein 3a when the pressure in the abdominal cavity 1 is higher than a predetermined value but the one-way valve 50 is closed to prevent blood from flowing out when the pressure in the abdominal cavity 1 is lower than the predetermined value.

Figure 1A:
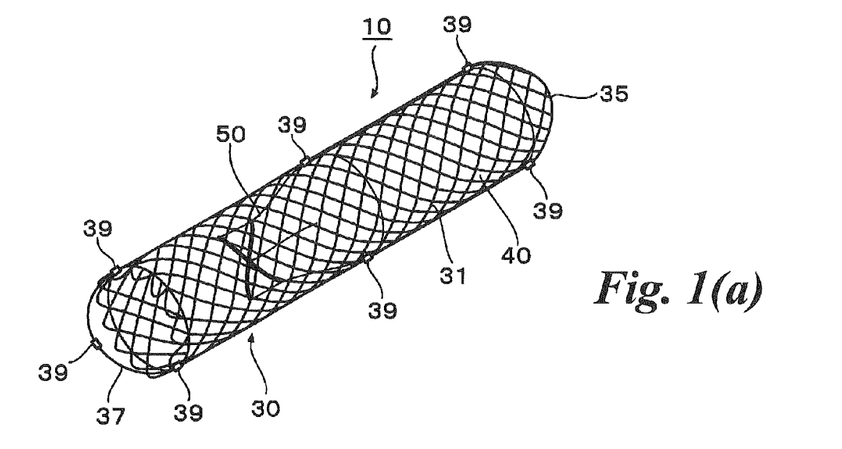
Figure 1B:
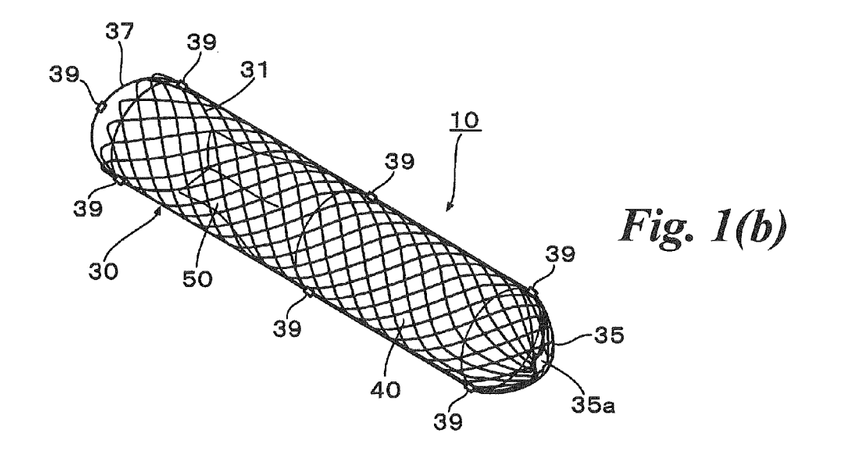
Figure 2B:
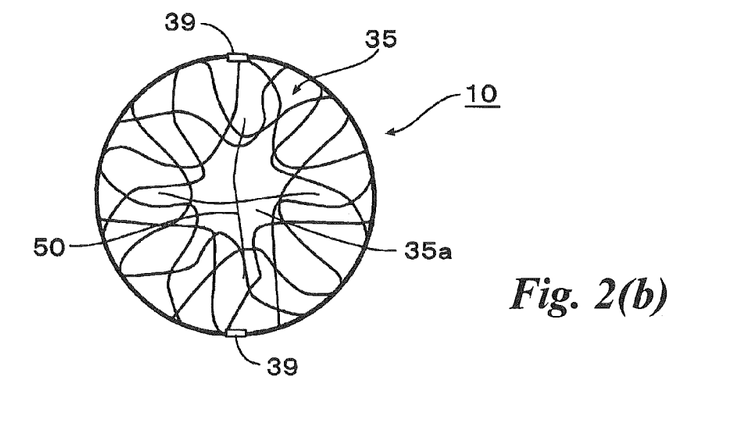
Figure 2C:
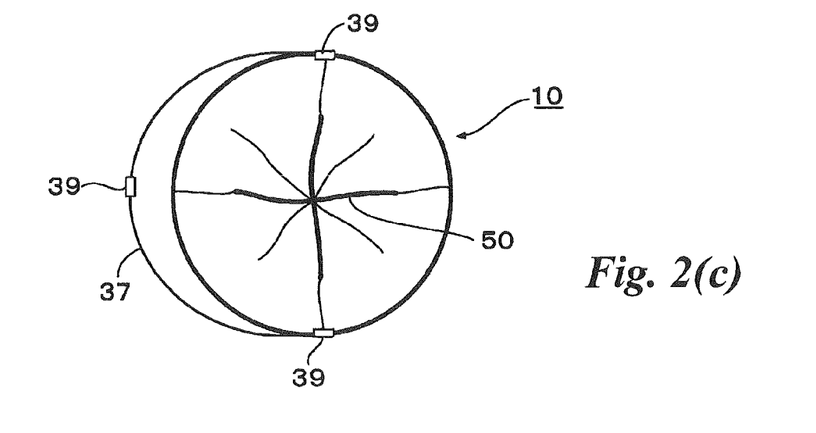

As shown in FIGS. 1(a) and 1(b) and FIG. 2(c), the one-way valve 50 in this embodiment is a so-called streamer valve. One end of the one-way valve 50 is cylindrically enlarged in diameter and connected to the cover member 40. The other end of the one-way valve 50 is formed like a cross when seen from side by causing circumferential edge portions to tightly contact with each other. Thus, the circumferential edge portions of the other end are normally closed. The one-way valve 50 is designed such that, when the differential pressure obtained by subtracting the pressure of the intrahepatic vein from the pressure in the abdominal cavity is not lower than a predetermined value due to accumulation of ascites, the other end circumferential edge portions of the one-way valve 50 are opened to drain ascites accumulated in the abdominal cavity 1 into the intrahepatic vein 3a as represented by the arrows C in FIG. 5(b). On the other hand, when the ascites is drained and the differential pressure is lower than the predetermined value, the other end circumferential edge portions of the one-way valve 50 are closed like a cross again.

The predetermined value of the differential pressure for opening the one-way valve 50 is set preferably in a range of 0 to 980 Pa, more preferably at a value in a range of 98 to 294 Pa.

The same synthetic resin as that of the cover member 40 can be used for the one-way valve 50. Although the one-way valve 50 and the cover member 40 are provided separately in this embodiment, the one-way valve 50 and the cover member 40 may be integrally formed from the same synthetic resin. The one-way valve 50 is not particularly limited. For example, the one-way valve 50 may be formed into a so-called flap valve shape in which a pair of thin belt-like pieces each having a predetermined length are laid to tightly contact with each other and longitudinally opposite side circumferential edges of the two pieces are welded, or may be formed as a beak-shaped valve structure in which a pair of plate-like curved pieces made of an elastic material are laid to tightly contact with each other.

An example of how to use the stent 10 according to the invention will be described below with reference to FIGS. 3 and 4. The stent 10 can be conveyed using a well-known conveyance jig or catheter. As the conveyance jig, for example, those described in JP-2009-201867-A and JP-2006-116184-A filed by the present applicant can be used. A method of placement using these conveyance jigs will be described below.

Although detailed description will be omitted, this type conveyance jib has an outer sheath, and an inner sheath disposed inside the outer sheath so as to be slidable. By sliding the outer sheath to the proximal side to open, then wrapping the stent 10 in the diametrically-contracted state on the outer circumference of the distal end of the inner sheath, and then sliding the outer sheath to the distal end side to close after and, the stent 10 in the diametrically-contracted state is held between the distal end of the inner sheath and the distal end of the outer sheath.

Then, by puncturing the subclavian vein 5 (see FIG. 3) with a puncture needle not shown, a guide wire not shown is inserted from a drilled hole of the puncture needle under the fluoroscope. That is, as represented by the arrow in FIG. 3, the guide wire is inserted into the intrahepatic vein 3a via the subclavian vein 5, the heart 6 and the vena cava 7 such that the distal end of the guide wire penetrates through the liver parenchyma 3b from the end of the intrahepatic vein 3a and protrudes into the abdominal cavity 1. In this state, the conveyance jig is inserted along the guide wire so as to pass through the liver parenchyma 3b via the subclavian vein 5, the heart 6, the vena cava 7 and the intrahepatic vein 3a such that the distal end portion of the conveyance member is placed in the abdominal cavity 1 under the fluoroscope in the same insertion path as that for the guide wire. Because the on-way valve 50 provided in the stent 10 according to this embodiment has a streamer valve structure in which one end is opened while the other end is narrowed, the guide wire can be inserted through the one-way valve 50.

Then, while the position of the stent 10 is visually recognized based on the markers 39 under the fluoroscope, positioning is performed suitably such that one end of the stent 10 is located in the intrahepatic vein 3a and the other end of the stent 10 is located in the abdominal cavity 1. In this state, by sliding the outer sheath of the conveyance jig to the proximal side, the stent 10 gradually expands in diameter by its own expanding force. By entirely releasing the stent 10 from the conveyance jig, as shown in a partially enlarged view of FIG.

Figure 4A:
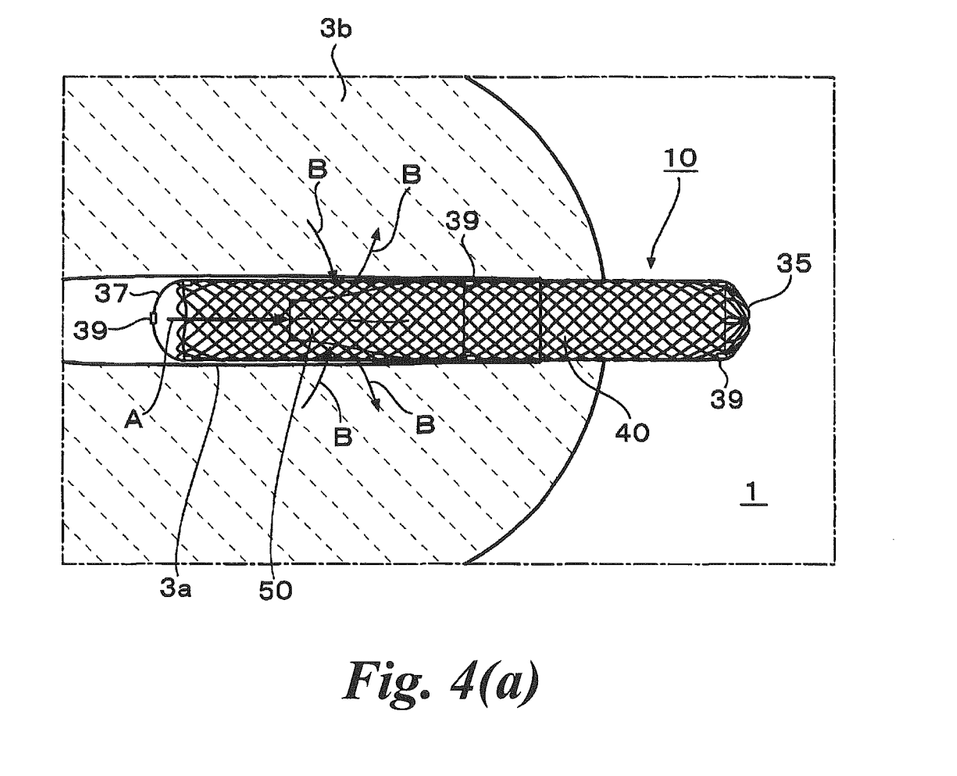
Figure 5A:
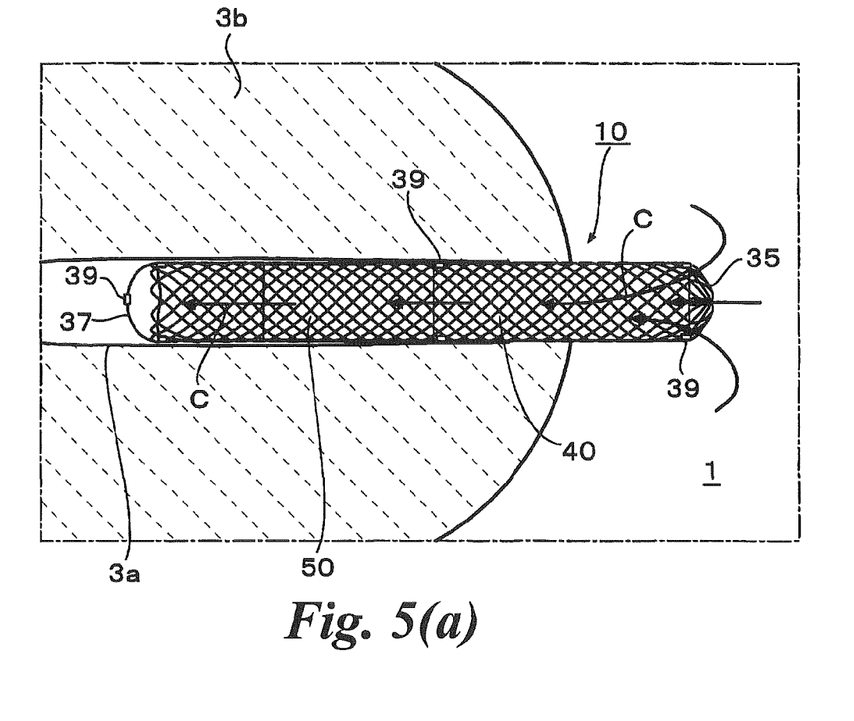

3, FIG. 4(a) and FIG. 5(a), the stent 10 can be placed in the state in the diametrically-expanded state such that one end thereof is held in the inner wall of the intrahepatic vein 3a so as to be disposed in the intrahepatic vein 3a, the other end thereof pierces the liver parenchyma 3b so as to be disposed in the abdominal cavity 1, and the cover member 40 is disposed in the liver parenchyma 3b.

The stent 10 merely requires that one end of the stent body 30 is disposed in the intrahepatic vein 3a while the other end of the stent body 30 pierces the liver parenchyma 3b so as to be disposed in the abdominal cavity 1. The stent 10 can be placed by an intravascular operation called IVR (Interventional Radiology) performed by a guide wire or a tubular stent insertion device without performing a large-scale operation such as an operation in which an insertion jig such as a tunneler necessary for placing the background-art abdominal cavity-vein shunt catheter is pushed through the hypodermis. Accordingly, the load imposed on the patient at the time of placement of the stent can be lightened.

As shown in FIG. 3, according to the stent 10, one end of the stent body 30 is disposed in the intrahepatic vein 3a while the other end of the stent body 30 is disposed in the abdominal cavity 1 relatively close to the liver 3. Thus, the stent 10 can be made relatively short in terms of length so that the load imposed on the patient after placement of the stent can be lightened compared with the case where the tubular catheter is placed.

Figure 5B:
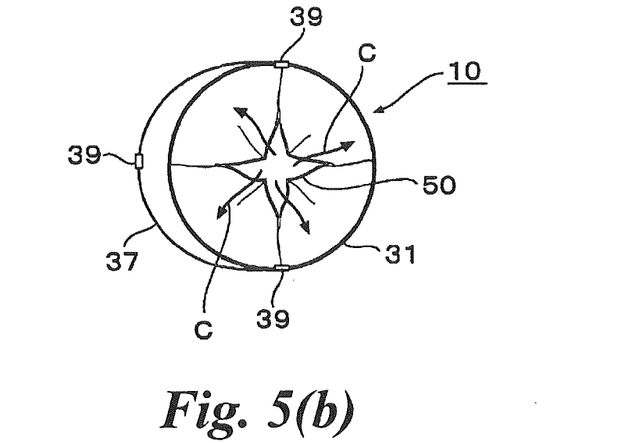

When the pressure in the abdominal cavity 1 exceeds a predetermined value because of accumulation of excessive ascites in the abdominal cavity 1 and the difference between the pressure of the intrahepatic vein 3a such that the pressure in the abdominal cavity 1 reaches the aforementioned value, the other end circumferential edge portions of the one-way valve 50 being closed like a cross are opened by being pressed by the high-pressure ascites, as shown in FIG. 5(b). Accordingly, ascites flows into the stent body 30 from the opening 35a and mesh-shaped openings of the entrance preventing member 35 and flows out to the intrahepatic vein 3a through the cover member 40 and the opened one-way valve 50 as represented by the arrows C in FIG. 5(a). Accordingly, excessive ascites accumulated in the abdominal cavity 1 can be surely transported.

Figure 4B:
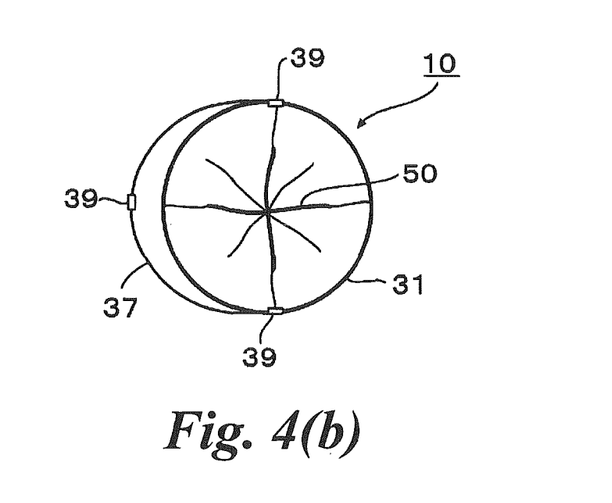

On the other hand, when the pressure in the abdominal cavity 1 becomes lower than the predetermined value because of the transportation of ascites into the intrahepatic vein 3a such that the pressure of the intrahepatic vein 3a is higher than the pressure in the abdominal cavity 1, the other end circumferential edge portions of the one-way valve 50 close like a cross again by the pressure difference, as shown in FIG. 4(b). Accordingly, ascites can be prevented from flowing out any more, and at the same time, the backflow as represented by the arrow A in FIG. 4(a) is prevented so that blood flowing in the intrahepatic vein 3a can be prevented from flowing out to the abdominal cavity 1 side.

One end of the stent 10 is disposed in the intrahepatic vein 3a while the other end thereof pierces the liver parenchyma 3b so as to be disposed in the abdominal cavity 1, and the one-way valve 50 is opened/closed suitably in accordance with the pressure change in the abdominal cavity 1. Thus, the pressure in the abdominal cavity 1 can be kept at a constant value so that the amount of ascites in the abdominal cavity 1 can be controlled to be a suitable amount.

According to the stent 10, the other end of the stent body 30 is disposed in the abdominal cavity 1. On this occasion, since the entrance preventing member 35 is provided in the other end side opening of the stent body 30, organs in the abdominal cavity 1, such as the intestinal tract moving relatively largely by peristalsis, can be prevented from entering the stent body 30. As a result, the inlet of ascites can be prevented from being blocked, and ascites can be made to flow into the stent body 30 smoothly.

Because the stent 10 is provided to pierce the liver parenchyma 3b, there is a possibility that the liver parenchyma 3b may enter the stent 10 from the openings of the mesh portion. In view of above, in this embodiment, because the cylindrical cover member 40 is disposed in the portion of the stent body 30 passing through the liver parenchyma 3b, that is, in the predetermined range from the entrance preventing member 35 side end portion of the stent body 30. Thus, since the openings of the mesh portion of the stent body 30 are covered with the cover member 40, the liver parenchyma 3b can be surely prevented from entering the stent body 30 through the openings of the mesh portion, and the flow path of ascites can be prevented from being blocked so that ascites can be made to flow smoothly.

Because the cover member 40 is disposed in the liver parenchyma passage portion of the stent body 30 but the cover member 40 is not disposed in other portions than the liver parenchyma passage portion of the stent body 30 such that the mesh portion of the stent body 30 is opened, fluid such as ascites, blood, etc. can flow through the openings. Thus, fluid can be prevented from being stagnated in a minute gap B (see FIG. 4(a)) between the inner circumference of the stent body 30 and the outer circumference of the one-way valve 50, and fluid can be made to flow smoothly. Particularly, since blood which easily coagulates can be accurately prevented from being stagnated, the coagulation of blood can be prevented effectively.

It is preferable that the stent 10 is recovered from the body when a disease causing ascites is cured and the amount of ascites becomes normal. In this case, the recovery handle 37 for stent recovery provided in the stent 10 can be used for recovering the stent 10 as follows. First, a recovery tube not shown is inserted through a guide wire or the like via the same insertion path as that of the conveyance jig such that the distal end portion of the recovery tube is disposed on a slightly more proximal side than the intrahepatic vein 3a side end portion of the stent 10.

In this state, a stent recovery jig having clamps shaped like scissors or a J-shaped hook provided at its distal end portion is inserted into the recovery tube and protruded from the distal end of the recovery tube. Then, when the clamps or the hook is suitably operated to be caught in the recovery handle 37 of the stent 10 and then the stent recovery jig is pulled to the proximal side, the stent body 30 can be diametrically contracted and received in the recovery tube. Then, by pulling out the recovery tube from the body, the stent 10 can be recovered.

In this manner, because the stent 10 according to this embodiment is provided with the recovery handle 37 for stent recovery, the stent 10 can be recovered through the recovery handle 37 when it is not necessary to transport ascites to the vein anymore.

Although the cover member 40 and the one-way valve 50 are provided separately and disposed individually on the inner circumferential side of the stent body 30 in this embodiment, the cover member 40 and the one-way valve 50 may be formed integrally and disposed on the inner circumferential side of the stent body 30. In this case, because the cover member 40 and the one-way valve 50 may be formed integrally, there is no seam etc. therebetween. Thus, sealing characteristic can be improved compared with the case where the two are formed separately and connected to each other, and fluidity of ascites can be improved. When the cover member 40 and the one-way valve 50 are formed integrally, the cover member 40 and the one-way valve 50 can be easily assembled in the stent body 30 compared with the case where the two are separately assembly in the stent body 30.

REFERENCE SIGNS LIST 1 abdominal cavity
3 liver
3a intrahepatic vein
3b liver parenchyma
10 abdominal cavity-vein shunt stent (stent)
30 stent body
31 wire
35 entrance preventing member
37 recovery handle
39 marker
40 cover member
50 one-way valve

The invention claimed is:

1. An abdominal cavity-vein shunt stent for transporting ascites accumulated in an abdominal cavity of a patient to a vascular system, including:
   a cylindrically-extending stent body having one end which is adapted to be disposed in an intrahepatic vein and the other end which is adapted to be disposed in the abdominal cavity by piercing a liver parenchyma;
   a one-way valve disposed on an inner circumference of the stent body and configured to have flow in a single direction based on a differential pressure so as to be opened to drain the ascites into the intrahepatic vein when a differential pressure obtained by subtracting a pressure of the intrahepatic vein from a pressure in the abdominal cavity is not lower than a predetermined value, and so as to be closed when the differential pressure is lower than the predetermined value, the stent-body covering an entire length of the one-way valve; and
   a cover member disposed in a portion of the stent body which is adapted to pass through the liver parenchyma from the intrahepatic vein to the abdominal cavity so that the liver parenchyma is prevented from entering the stent body,
   wherein the one-way valve is integrally formed with the cover member at a side thereof which is adapted to be disposed in the intrahepatic vein, and the one-way valve and the cover member are disposed on the inner circumference of the stent body,
   wherein the cover member is not disposed in a portion of the stent body on an outer circumference of the one-way valve,
   wherein the portion of the stent body in which the cover member is not disposed is mesh-shaped, and is opened when the one-way valve is closed,
   wherein an outer diameter of the one-way valve is separated from an inner diameter of the stent body when the one-way valve is in a closed state,
   wherein the outer diameter of the one-way valve is closer to the inner diameter of the stent body when the one-way valve is in an opened state,
   wherein an entirety of the stent body has a constant diameter, and
   wherein an entrance preventing member of mesh adapted to prevent organs in the abdominal cavity from entering the stent body is provided over an opening of the other end of the stent body which is adapted to be disposed in the abdominal cavity.

2. The abdominal cavity-vein shunt stent of claim 1, wherein a stent recovery handle is provided at the one end of the stent body which is adapted to be disposed in the intrahepatic vein.

3. The abdominal cavity-vein shunt stent of claim 1, wherein the predetermined value of the differential pressure for opening the one-way valve is set in a range of 0 to 980 Pa.

4. The abdominal cavity-vein shunt stent of claim 1, wherein the predetermined value of the differential pressure for opening the one-way valve is set in a range of 98 to 294 Pa.

5. The abdominal cavity-vein shunt stent of claim 1, further comprising markers of a radiopaque metal.

6. The abdominal cavity-vein shunt stent of claim 1, wherein a total length of the stent body is in a range of 20 to 100 mm.

7. The abdominal cavity-vein shunt stent of claim 1, wherein a total length of the stent body is in a range of 40 to 50 mm.

8. The abdominal cavity-vein shunt stent of claim 1, wherein an outer diameter of the stent body is in a range of 3 to 15 mm.

9. The abdominal cavity-vein shunt stent of claim 1, wherein an outer diameter of the stent body is in a range of 5 to 7 mm.

10. The abdominal cavity-vein shunt stent of claim 1, wherein the stent body comprises a flexible material.

11. The abdominal cavity-vein shunt stent of claim 1, wherein the entrance preventing member is narrowed while extending in an axial direction from a circumferential edge of the other end of the stent body.

12. The abdominal cavity-vein shunt stent of claim 1, wherein the one-way valve does not protrude from the one end and the other end of the stent body.

* * * * *